United States Patent
Manabe et al.

(10) Patent No.: US 10,639,211 B2
(45) Date of Patent: May 5, 2020

(54) METHOD FOR MANUFACTURING UNDERPANTS-TYPE DISPOSABLE DIAPER, AND UNDERPANTS-TYPE DISPOSABLE DIAPER

(71) Applicant: DAIO PAPER CORPORATION, Ehime (JP)

(72) Inventors: Sadanao Manabe, Tokyo (JP); Yosuke Mori, Ehime (JP); Takashi Hagi, Ehime (JP)

(73) Assignee: DAIO PAPER CORPORATION, Ehime (JP)

(*) Notice: Subject to any disclaimer, the term of this patent is extended or adjusted under 35 U.S.C. 154(b) by 737 days.

(21) Appl. No.: 15/315,277

(22) PCT Filed: Jun. 18, 2015

(86) PCT No.: PCT/JP2015/067644
§ 371 (c)(1),
(2) Date: Nov. 30, 2016

(87) PCT Pub. No.: WO2015/198967
PCT Pub. Date: Dec. 30, 2015

(65) Prior Publication Data
US 2017/0196738 A1    Jul. 13, 2017

(30) Foreign Application Priority Data

Jun. 24, 2014 (JP) ................ 2014-129602

(51) Int. Cl.
*A61F 13/15* (2006.01)
*A61F 13/20* (2006.01)
(Continued)

(52) U.S. Cl.
CPC ........ *A61F 13/15601* (2013.01); *A61F 13/15* (2013.01); *A61F 13/15723* (2013.01);
(Continued)

(58) Field of Classification Search
CPC .... A61F 13/15; A61F 13/15739; A61F 13/49; A61F 13/49009; A61F 13/496;
(Continued)

(56) References Cited

U.S. PATENT DOCUMENTS 8,771,449 B2    7/2014 Takino et al.
8,894,798 B2    11/2014 Sakaguchi et al.
(Continued)

FOREIGN PATENT DOCUMENTS

EP      2387982 A1   11/2011
JP   2007-181543 A    7/2007
(Continued)

*Primary Examiner* — Michele M Kidwell
(74) *Attorney, Agent, or Firm* — Muncy, Geissler, Olds & Lowe, PC

(57) ABSTRACT

Resilient and elastic members are sandwiched between a first sheet material and a second sheet material and overlapping areas of the first sheet material and the second sheet material are not joined together at CD direction both end portions but are joined together at an area between the both end portions, thereby to form a belt-like continuous elastic belt. The elastic belt is cut in the middle of a CD direction thereof between the resilient and elastic members at a joined position of the first sheet material and the second sheet material to form a pair of divided elastic belt. CD direction positions of these divided elastic belts are exchanged or the divided elastic belts are vertically reversed. A ventral side outer body and a dorsal side outer body are formed from the pair of divided elastic belts.

5 Claims, 11 Drawing Sheets

(51) Int. Cl.
- *A61F 13/496* (2006.01)
- *A61F 13/49* (2006.01)
- *B29C 65/48* (2006.01)
- *B29C 65/00* (2006.01)
- *B29K 23/00* (2006.01)
- *B29K 105/00* (2006.01)
- *B29L 31/48* (2006.01)

(52) U.S. Cl.
CPC .. *A61F 13/15739* (2013.01); *A61F 13/15764* (2013.01); *A61F 13/49* (2013.01); *A61F 13/496* (2013.01); *A61F 13/49009* (2013.01); *B29C 65/4815* (2013.01); *B29C 66/472* (2013.01); *B29C 66/7294* (2013.01); *B29C 66/735* (2013.01); *A61F 13/4963* (2013.01); *A61F 2013/49092* (2013.01); *B29K 2023/00* (2013.01); *B29K 2105/256* (2013.01); *B29L 2031/4878* (2013.01)

(58) Field of Classification Search
CPC ........... A61F 13/4963; A61F 13/15601; B29C 65/4815; B29K 2105/256; B29L 2031/4878

See application file for complete search history.

(56) References Cited

U.S. PATENT DOCUMENTS

| | | |
|---|---|---|
| 8,945,081 B2 | 2/2015 | Takino |
| 2011/0288517 A1* | 11/2011 | Mori ................. A61F 13/15756 604/385.3 |
| 2012/0024452 A1 | 2/2012 | Sakaguchi et al. |
| 2012/0226254 A1 | 9/2012 | Takino |

FOREIGN PATENT DOCUMENTS

| | | |
|---|---|---|
| JP | 2009-061045 A | 3/2009 |
| JP | 2009-160129 A | 7/2009 |
| JP | 2010-158590 A | 7/2010 |
| JP | 2011-115229 A | 6/2011 |
| WO | WO 2010/074064 A1 | 7/2010 |

* cited by examiner

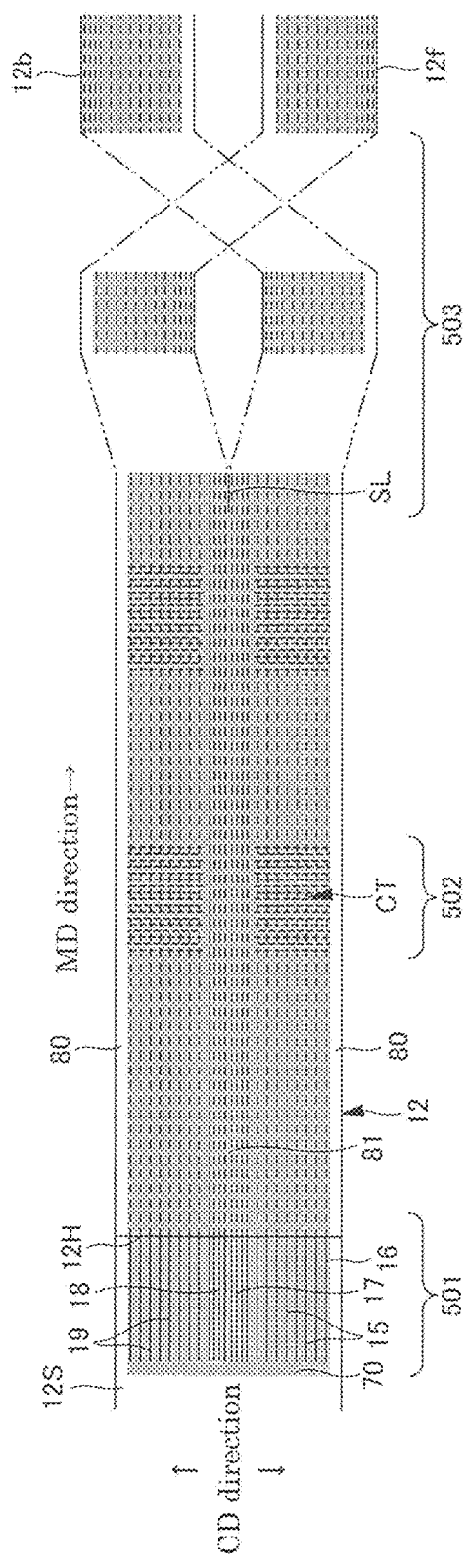
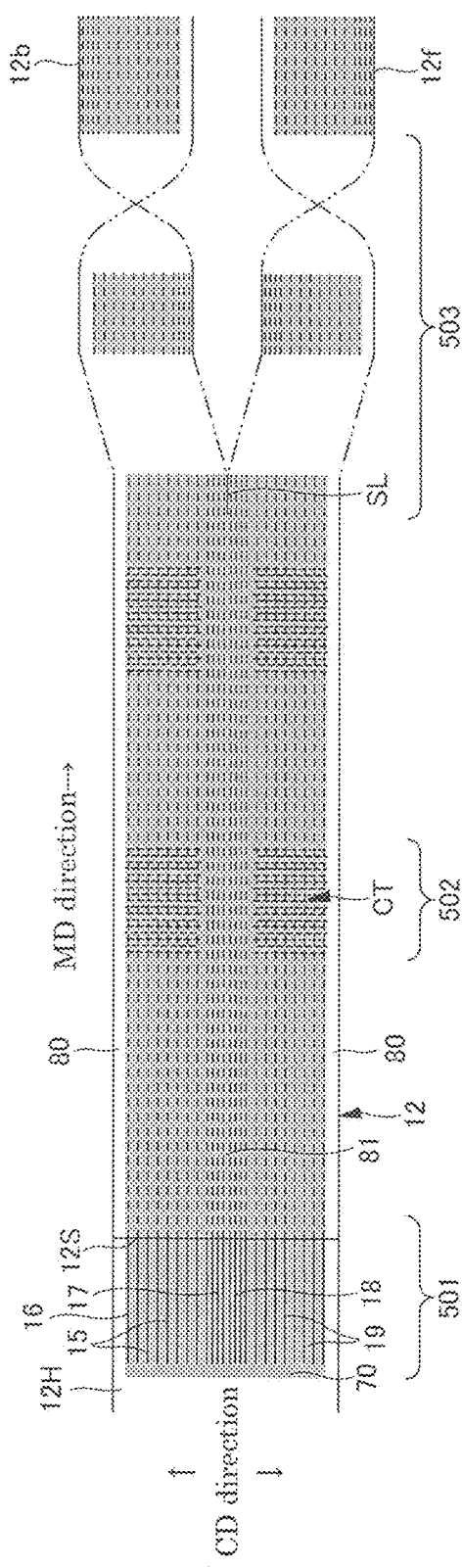
FIG.1(a)
FIG.1(b)

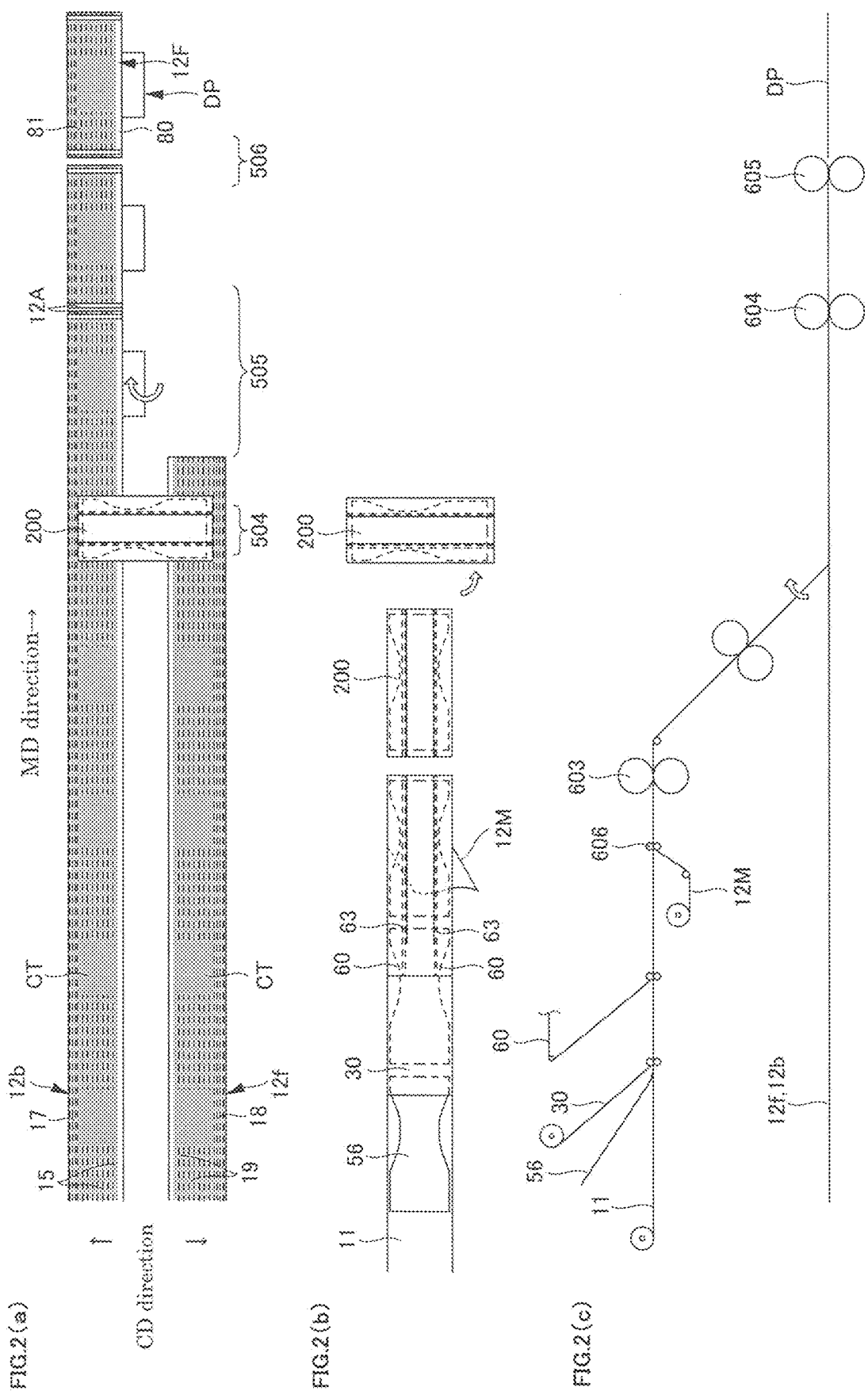

METHOD FOR MANUFACTURING UNDERPANTS-TYPE DISPOSABLE DIAPER, AND UNDERPANTS-TYPE DISPOSABLE DIAPER

TECHNICAL FIELD

The present invention relates to a production method for an underpants-type disposable diaper and an underpants-type disposable diaper.

BACKGROUND ART

As a form of an underpants-type disposable diaper, there is known an underpants-type disposable diaper including: a cylindrical outer body that is formed by joining a ventral side outer body and a dorsal side outer body at both sides; and an inner body that has a front part joined to a width direction central area of the ventral side outer body and a back part joined to a width direction central area of the dorsal side outer body and passes through the crotch portion of a wearer, the ventral side outer body and the dorsal side outer body being separated without being continued (for example, refer to Patent Document 1). In such an outer halved type, the ventral side outer body and the dorsal side outer body are not continued but separated at the crotch side, which provides an advantage that there is no need to punch leg openings for passage of the wearer's legs, or if there is a need, only small-area leg openings is enough. That is, as cut pieces (hereinafter, also called trims) are discarded, the material loss (hereinafter, also called trim loss) can be suppressed.

As a method for manufacturing the outer halved-type diapers, in general, the ventral side outer body and the dorsal side outer body are separately fabricated from belt-like continuous sheet materials, and the form illustrated in FIG. 1 of Patent Document 1 is also categorized as this method. In this case, it is necessary to provide an assembly line for the ventral side outer body and an assembly line for the dorsal side outer body in parallel to convey the outer bodies in parallel, which makes the production facilities larger and more complicated. This problem can be solved by supplying one belt-like continuous sheet material in a MD direction (mechanical direction or conveyance direction. The lateral direction orthogonal to this direction is called a CD direction) and disposing resilient and elastic members on the sheet material, and folding back the sheet material to cover the resilient and elastic members, then cutting the sheet material continuously in the direction parallel to the MD direction to divide the sheet material into a ventral side elastic belt and a dorsal side elastic belt, and then conveying the belts separated from each other in parallel in a width direction as described in paragraph 0037, Patent Document 1. In this case, however, at the step of folding back the sheet material, the wide sheet material is folded into two. This is not only making the folding facility (sailor) larger but causing a problem that it is difficult to fold the sheet material neatly without wrinkles. In addition, the edge of the waist of either the ventral side outer body or the dorsal side outer body may not make a fold in the sheet material (excellent in texture without turn-up of the sheet material) but may deteriorate in texture and appearance. Additionally, as described in Patent Document 1, when the wide sheet material is folded into two, the edges of the sheet material are likely to be misaligned, and the misalignment remains at the edge of the waist of the diaper to contribute to deterioration in texture and appearance.

There is known another method for manufacturing the ventral side outer body and the dorsal side outer body by adhering two sheet materials to each other by a hot-melt adhesive and then separating them into two as illustrated in FIG. 4 of Patent Document 3. According to this method, when the two sheet materials are bonded by the hot-melt adhesive, some non-bonded portions would be formed at the end portions for the reason that it is difficult to bond the CD direction both ends of the sheet materials and the like. However in Patent Document 3, by making one of the sheet materials wider than the other in the CD direction and by folding back the extending portions so as to be bonded on the opposite side, such non-bonded portions are not left anymore.

However, when the extending portions are not folded unlike in Patent Document 3 for simpler and lower-cost manufacture, the non-bonded portions described above are positioned at the waist end portions of the ventral side outer body and the dorsal side outer body. Accordingly, it is not possible to provide resilient and elastic members at the waist end portions, thereby resulting in insufficient fit of the waist end portions. In addition, in that case, the sheet materials spread out at the non-bonded portions of the waist end portions to degrade appearance, and the non-bonded portions of the waist end portions are folded inward when the user is wearing the diaper, which may deteriorate the fit of the diaper.

CITATION LIST

Patent Document

Patent Document 1: JP-A No. 2009-061045
Patent Document 2: JP-A No. 2009-160129
Patent Document 3 JP-A No. 2010-158590

SUMMARY OF INVENTION

Technical Problem

A main object of the present invention is to structure simply the ventral side outer body and the dorsal side outer body without folding the sheet materials and prevent reduction in the fit of the waist end portions and the like.

Solution to Problem

The present invention for solving the foregoing problems is as follows:
<The Invention of Claim 1>
A method for manufacturing an underpants-type disposable diaper comprising:
an outer body that is formed by joining both side parts of a ventral side outer body and both side parts of a dorsal side outer body; and
an inner body that has a front part joined to a width-direction central area of the ventral side outer body and a back part joined to a width-direction central area of the dorsal side outer body respectively and passes through a crotch portion of a wearer, the ventral side outer body and the dorsal side outer body being not continued but separated at a crotch side, wherein
a belt-like continuous first sheet material is supplied in a direction of continuity thereof,
resilient and elastic members for imparting elasticity to the ventral side outer body and the dorsal side outer body are disposed on the first sheet material, a belt-like continuous second sheet material is supplied in a direction of continuity thereof on the resilient and elastic members in the first sheet material to sandwich the resilient and elastic members between the first sheet material and the second sheet material, and overlapping areas of the first sheet material and the second sheet material are not joined together at CD direction both end portions but are joined together at an area between the both end portions to form a belt-like continuous elastic belt, the elastic belt is cut in the middle of a CD direction thereof at a joined position of the first sheet material and the second sheet material to form a pair of divided elastic belt, and CD direction positions of these divided elastic belts are exchanged or the divided elastic belts are vertically reversed respectively, and the diaper is manufactured such that one of the pair of divided elastic belts is set as the ventral side outer body and the other is set as the dorsal side outer body.

(Operation and Effect)

The present invention is the same as that described in Patent Document 3 in that the first sheet material and the second sheet material are bonded and then divided to form the ventral side and dorsal side elastic belts, but the present invention does not include folding of the sheet materials. When the sheet materials are not simply folded, non-joined portions are formed at the waist end portions to deteriorate the fit of the waist end portions and the like as described above. According to the present invention, however, the elastic belt is divided at the joined position of the first sheet material and the second sheet material, and after the division of the elastic belt, the CD direction positions of the divided elastic belts are exchanged or the divided elastic belts are vertically reversed. Accordingly, in the manufactured underpants-type disposable diaper, the waist edges of the ventral side outer body and the dorsal side outer body are composed of the cut edges of the divided elastic belts, and the first sheet material and the second sheet material are joined up to the edges. Meanwhile, the non-joined portions of the elastic belts are positioned at end portions of leg openings in the ventral side outer body and the dorsal side outer body.

Accordingly, in the present invention, the first sheet material and the second sheet material can be joined together up to the waist edges of the ventral side outer body and the dorsal side outer body. This makes it possible to provide the resilient and elastic members at the waist end portions of the ventral side outer body and the dorsal side outer body, thereby preventing reduction in the fit of the waist end portions. In addition, for the same reason, it is possible to prevent degradation in appearance caused by the spread of the sheet materials at the waist end portions and deterioration in fit caused by inward folding of the waist end portions when the user is wearing the diaper. Meanwhile, in the manufactured underpants-type disposable diaper, the non-joined portions of the first sheet material and the second sheet material are positioned at the end portions of the leg openings in the ventral side outer body and the dorsal side outer body. These end portions are positioned around the legs of the wearer and are essential to have following capability and flexibility in response to the wearer's large motion unlike the waist-side end portions. Accordingly, the presence of the non-joined portions, that is, the presence of the portions not hardened by joining is conversely advantageous. This makes it possible to obtain the effect of alleviating rash and abrasion in the wearer's body caused by contact.

<The Invention of Claim 2>

The method for manufacturing an underpants-type disposable diaper according to claim 1, wherein the first sheet material and the second sheet material are joined together by a hot-melt adhesive.

(Operation and Effect)

As described above, when the first sheet material and the second sheet material are joined together by a hot-melt adhesive, it is difficult to bond them up to the CD direction both ends, thereby to form inevitably non-joined portions at the end portions. Accordingly, the present invention is preferred in particular in the case of joining the first sheet material and the second sheet material by the use of a hot-melt adhesive.

<The Invention of Claim 3>

The method for manufacturing an underpants-type disposable diaper according to claim 1 or 2, wherein the first sheet material and the second sheet material are equal in CD direction width.

(Operation and effect)

When the first sheet material and the second sheet material are equal in CD direction width, it is difficult in particular to join the two up to the CD direction both ends. Accordingly, the present invention is especially preferred in that case.

<The Invention of Claim 4>

An underpants-type disposable diaper comprising:

an outer body that is formed by joining both side parts of a ventral side outer body and both side parts of a dorsal side outer body; and an inner body that has a front part joined to a width-direction central area of the ventral side outer body and a back part joined to a width-direction central area of the dorsal side outer body and passes through a crotch portion of a wearer, the ventral side outer body and the dorsal side outer body being not continued but separated at a crotch side, wherein the ventral side outer body and the dorsal side outer body have a first sheet material and a second sheet material that extend from their waist-side edges to leg opening edges without being folded and resilient and elastic members that are provided between the first sheet material and the second sheet material, at leg opening-side end portions of the ventral side outer body and the dorsal side outer body, the resilient and elastic members are not provided between the first sheet material and the second sheet material, and the first sheet material and the second sheet material are not joined together, and at waist-side end portions of the ventral side outer body and the dorsal side outer body, the resilient and elastic members are provided between the first sheet material and the second sheet material, the waist-side edges of the first sheet material and the second sheet material coincide with each other, and the first sheet material and the second sheet material are joined up to the waist-side edges.

(Operation and Effect)

The invention of claim 4 provides the same operation and effect as those of the invention of claim 1. Specifically, in the underpants-type disposable diaper of the present invention, the first sheet material and the second sheet material are joined together up to the waist edges of the ventral side outer body and the dorsal side outer body. This makes it possible to provide the resilient and elastic members at the waist end portions of the ventral side outer body and the dorsal side outer body, thereby preventing reduction in the fit of the waist end portions. In addition, for the same reason, it is possible to prevent degradation in appearance caused by the spread of the sheet materials at the waist end portions and deterioration in fit caused by inward folding of the waist end portions when the user is wearing the diaper.

Meanwhile, the leg opening-side end portions of the ventral side outer body and the dorsal side outer body are non-joined portions.

These end portions are positioned around the legs of the wearer and are essential to have following capability and flexibility in response to the wearer's large motion unlike the waist-side end portions. Accordingly, the presence of the non-joined portions, that is, the presence of the portions not hardened by joining is conversely advantageous. This makes it possible to obtain the effect of alleviating rash and abrasion in the wearer's body caused by contact.

<The Invention of Claim 5>

The underpants-type disposable diaper according to claim 4, wherein the joining is made by a hot-melt adhesive.

(Operation and Effect)

The invention of claim 5 provides the same operation and effect as those of the invention of claim 2.

Advantageous Effects of Invention

As described above, according to the present invention, it is possible to provide the advantages of structuring simply the ventral side outer body and the dorsal side outer body without folding the sheet materials and preventing reduction in the fit of the waist end portions and the like.

BRIEF DESCRIPTION OF DRAWINGS

FIGS. 1 (a) and 1(b) are schematic views of a manufacturing process flow;

FIGS. 2 (a) to 2(c) are schematic views of the manufacturing process flow;

DESCRIPTION OF EMBODIMENTS

Figure 3:
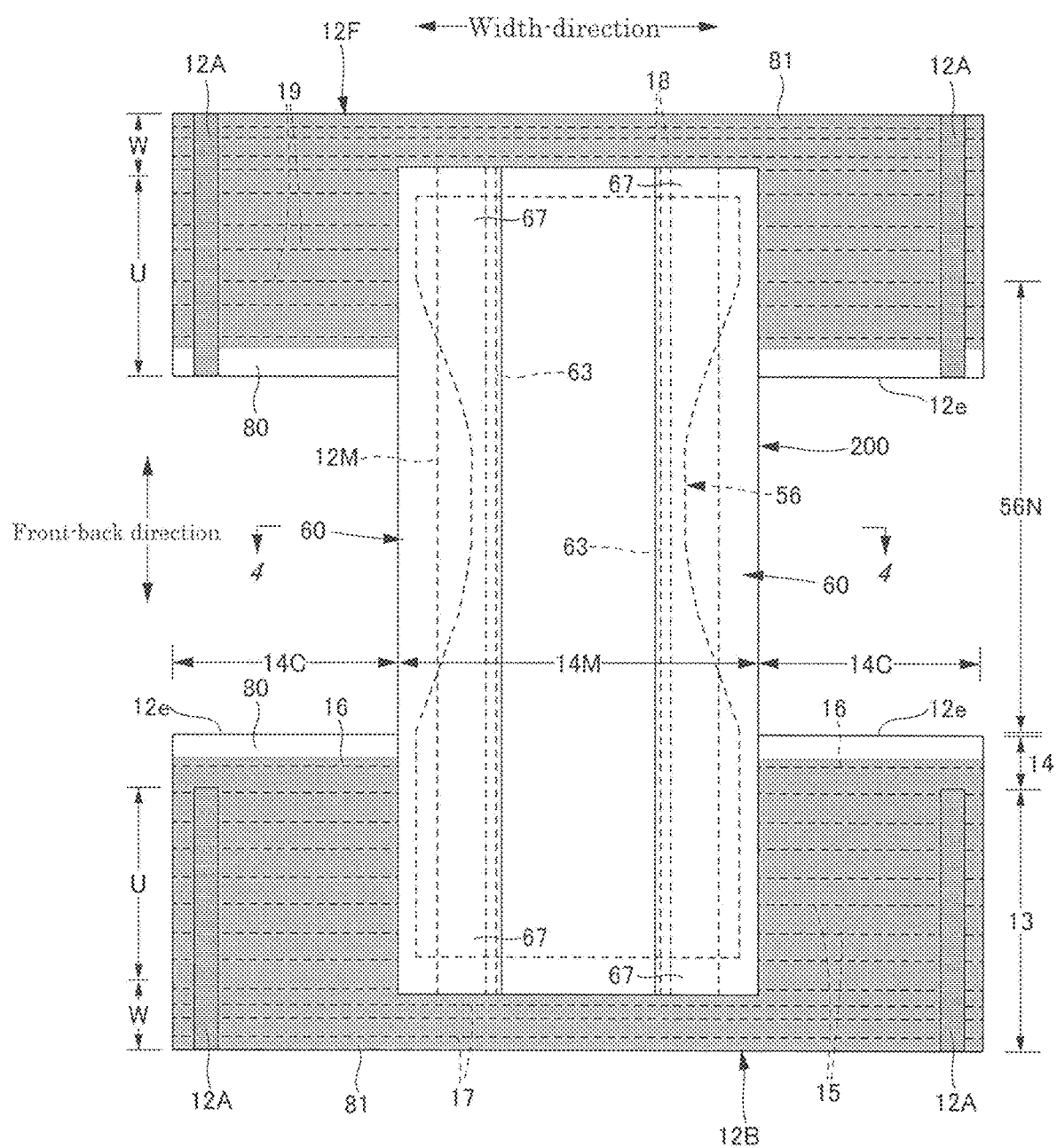
FIG. 3 is a planar view of an inner surface of an underpants-type disposable diaper in an opened state.

Embodiments of the present invention will be described below in detail.

<About a Manufacturing Method>

FIGS. 1 and 2 illustrate an example of a manufacturing process flow that has mainly an elastic belt formation step 501, a resilient and elastic member cutting step 502, an elastic belt division and arrangement changing step 503, an inner body attachment step 504, a side part joining step 505, and a cutoff step 506. More specifically, FIG. 1(a) illustrates an example of an outer body assembly step in a main assembly line, and FIG. 1(b) illustrates another example. The planar view of FIG. 2(a) illustrates the inner body attachment step and the subsequent steps in the main assembly line, the planar view of FIG. 2(b) illustrates an inner body assembly line, and the front view of FIG. 2(c) illustrates both the main assembly line and the inner body assembly line.

First, at the elastic belt formation step 501 in the main assembly line, a first sheet material 12S and a second sheet material 12H with widths of the ventral side outer body and the dorsal side outer body are supplied. While the first sheet material 12S and the second sheet material 12H are conveyed along a direction of continuity, a hot-melt adhesive is applied to at least one of opposed surfaces of the first sheet material 12S and the second sheet material 12H. Then, while the first sheet material 12S and the second sheet material 12H are bonded to each other, a large number of elongated resilient and elastic members 15 to 19 are continuously sandwiched between the first sheet material 12S and the second sheet material 12H at CD direction intervals in an MD direction extended state. The resilient and elastic members 15 to 19 are fixed by a hot-melt adhesive 70 to the first sheet material 12S and the second sheet material 12H to form a belt-like continuous elastic belt 12. Instead of the elongated resilient and elastic members 15 to 19, sheet-like or net-like resilient and elastic members may be provided partially or entirely in the area of the large number of elongated resilient and elastic members 15 to 19.

Characteristically, at the time of adhesion of the first sheet material 12S and the second sheet material 12H, in the overlapping area of the first sheet material 12S and the second sheet material 12H, the CD direction both end portions are set as non-joined portions 80 in which the first sheet material 12S and the second sheet material 12H are not continuously joined in the MD direction, and the CD direction area between the non-joined portions is set as a joined portion 81 in which the first sheet material 12S and the second sheet material 12H are joined continuously or intermittently in the MD direction and joined continuously or intermittently in the CD direction by a hot-melt adhesive. The CD direction width of the non-joined portions 80 can be arbitrarily set but is desirably set to about 3 to 50 mm, more desirably 5 to 15 mm. The reason will be described later.

The method of applying the hot-melt adhesive for formation of the joined portion 81 can be decided as appropriate according to the joint pattern. For example, to apply the hot-melt adhesive to almost the entire joined portion 81, surface application methods such as curtain application, slot application, and spray application, or intermittent application methods such as spiral application, summit application, and pattern application (relief method or transfer method) can be preferably used. To apply the adhesive in a vertical stripe pattern in which the adhesive is intermittent in the MD direction or in a dot pattern in which the adhesive is intermittent in the MD direction and the CD direction, a pattern application method or a dot application method is preferred. To apply the adhesive in a lateral stripe pattern in which the adhesive is intermittent only in the CD direction, such an application method as bead application, slot application, or spray application is preferred.

When the first sheet material 12S and the second sheet material 12H are joined by the use of the hot-melt adhesive 70, it is difficult to bond them up to the CD direction both ends and the non-joined portions 80 are inevitably formed at the end portions as described above. Accordingly, the present invention is preferred in particular in the case of joining the first sheet material 12S and the second sheet material 12H by the use of the hot-melt adhesive 70. Instead of the hot-melt adhesive 70, the first sheet material 12S and the second sheet material 12H may be bonded by a joining means including welding the sheet materials such as ultrasound sealing or heat sealing.

The resilient and elastic members 15 to 19 may be fixed to the first sheet material 12S and the second sheet material 12H by the means for joining the first sheet material 12S and the second sheet material 12H. In addition to or instead of this, the first sheet material 12S and the second sheet material 12H may be fixed by the dedicated hot-melt adhesive 70. In this case, the hot-melt adhesive 70 may be applied to the outer peripheral surfaces of the resilient and elastic members 15 to 19 (by the use of a comb gun or a sure-wrap nozzle) or the hot-melt adhesive 70 may be applied to at least one of the first sheet material 12S and the second sheet material 12H in positions where the resilient and elastic members 15 to 19 are to be fixed. In particular, it is desired that the end portions of the resilient and elastic members 15 to 19 in the final product are bonded and fixed by the hot-melt adhesive 70 to the first sheet material 12S and the second sheet material 12H.

Next, at the resilient and elastic member cutting step 502, the resilient and elastic members 15 and 19 positioned in a part CT of the formed elastic belt overlapping an inner body 200 are cut by a cutting device such as a heat emboss so that no stretching force of the resilient and elastic members 15 and 19 act on the part CT. The cutting step 502 may be performed as necessary and may be omitted.

Next, at the elastic belt division and arrangement changing step 503, the formed elastic belt 12 is cut by a slitter at a position of a boundary between the ventral side and the dorsal side in the middle of the CD direction thereof (between the ventral side resilient and elastic members 18 and 19 and the dorsal side resilient and elastic members 15 to 17) and at a joint position SL of the first sheet material 12S and the second sheet material 12H to form a pair of divided elastic belts 12f and 12b. Characteristically, the CD direction positions of the divided elastic belts 12f and 12b are exchanged as illustrated in FIG. 1(a) or the divided elastic belts 12f and 12b are vertically reversed as illustrated in FIG. 1(b) so that the CD direction central edges of the divided elastic belts 12f and 12b are positioned outside in the CD direction and the CD direction outer edges of the same are positioned on the CD direction central side. In that state, the divided elastic belts 12f and 12b are supplied to the inner body attachment step 504.

In this example, between the division of the elastic belt 12 and the inner body attachment step 504, the CD direction space between the divided elastic belts 12f and 12b can be adjusted to the position of attachment to the inner body 200 described later according to the entire length of the diaper as necessary. However, when the CD direction space between the divided elastic belts 12f and 12b matches the position of attachment to the inner body 200 without having to make such a position adjustment, the position adjustment can be omitted to maintain the CD direction space. In addition, between the division of the elastic belt 12 and the inner body attachment step 504, the end portions of the divided elastic belts 12f and 12b to be the leg openings can be cut as necessary in a curve shape along the legs.

As understood from the elastic belt division and arrangement changing step 503 in the manufacturing method, the cutting positions are on the waist side and the CD direction both ends are on the leg-opening side because the arrangement of the divided elastic belts 12f and 12b are changed. In accordance with this, the resilient and elastic members 17 and 18 on the waist part are attached on the cutting position side in the middle of the CD direction thereof, and the resilient and elastic members 15 and 19 on the lower waist portion are attached to the CD direction both end portions (opposite to the positions according to the conventional manufacturing method).

The following steps can be performed according to the publicly known method. Specifically, in the example illustrated in FIG. 2, in a manufacturing line of the inner body 200, a continuous belt-like liquid-impervious sheet 11 is fed, an absorber 56 and a liquid-pervious top sheet 30 are stacked in this order on the liquid-impervious sheet 11, and the both sides of the top sheet 30 are wrapped around to the back side of the liquid-impervious sheet 11 and fixed by a hot-melt adhesive or the like. Next, belt-like three-dimensional gather belts 60 in which elastic members 63 are fixed to the CD direction central-side end portions of the base material in the MD direction extended state are supplied to the CD direction (line transverse direction) both sides of the sheet. The CD direction outer side parts of the three-dimensional gather belts 60 are wrapped around to the back side of the sheet 11 beyond the wrap-around part of the top sheet and fixed by a hot-melt adhesive or the like. The CD direction central side parts are fixed by a hot-melt adhesive or the like to the side parts of the top sheet 30 on the MD direction both end portions of the front side of the part to be individual inner bodies. Next, a continuous belt-like outer body for inner body 12M is supplied to the back side of the liquid-impervious sheet 11 and the three-dimensional gather belts 60 by an outer body for inner body attachment roll 606 and is adhered to them continuously by a hot-melt adhesive or the like. After that, the sheet is cut at MD direction intervals by an inner body cutoff device 603 to form the individual inner bodies 200. The inner bodies 200 are rotated such that the front-back direction is in parallel to the CD direction, and they are supplied to the inner body attachment step 504.

At the inner body attachment step 504, the inner body 200 supplied from the inner body manufacturing line is adhered at MD direction intervals to a pair of continuous belt-like divided elastic belts conveyed in sequence at CD direction intervals by a hot-melt adhesive or the like.

Then, at the subsequent side part joining step 505, the pair of divided elastic belts is folded in such a manner as to overlap one side and the other side in CD direction, subjected to a joining process at MD direction predetermined intervals by a joining device 604 such as a heat seal, and joined together at parts 12A as width-direction both side parts of an individual diaper DP. After that, at the final cutoff step 506, the sheet is cut by a diaper cutoff device 605 at MD direction predetermined intervals along a boundary between individual diapers (positioned between a joining part 12A of one of the adjacent diapers and a joining part 12A of the other diaper), thereby obtaining the individual diapers.

According to the foregoing manufacturing method, the elastic belt 12 is divided at a joining position SL between the first sheet material 12S and the second sheet material 12H, and after the division, the CD direction positions of the divided elastic belts 12f and 12b are exchanged or the divided elastic belts 12f and 12b are vertically reversed. Accordingly, in the manufactured underpants-type disposable diaper, the waist edges of a ventral side outer body 12F and a dorsal side outer body 12B are formed from the cut edges of the divided elastic belts 12f and 12b, and the first sheet material 12S and the second sheet material 12H are joined together up to the edges. Meanwhile, the non-joined portions 80 of the elastic belt 12 are positioned at the leg-opening end portions of the ventral side outer body 12F and the dorsal side outer body 12B.

Figure 8:
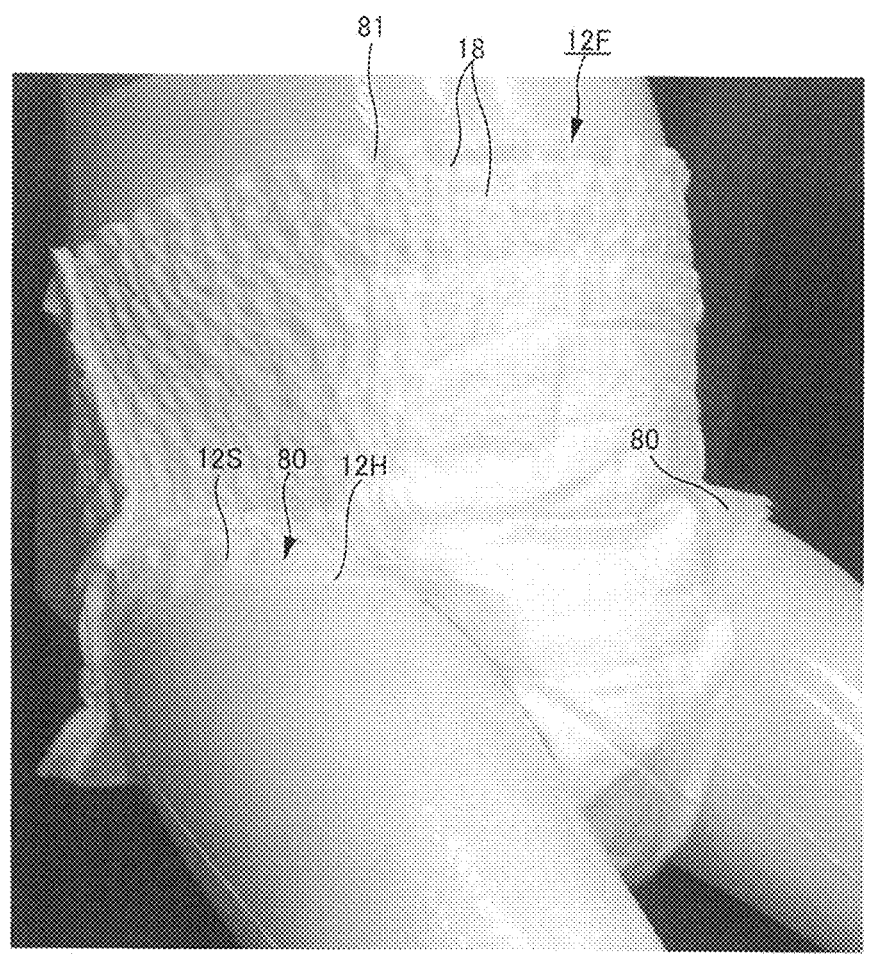
FIG. 8 is a photograph of a product sample put on a dummy doll.
Figure 9:
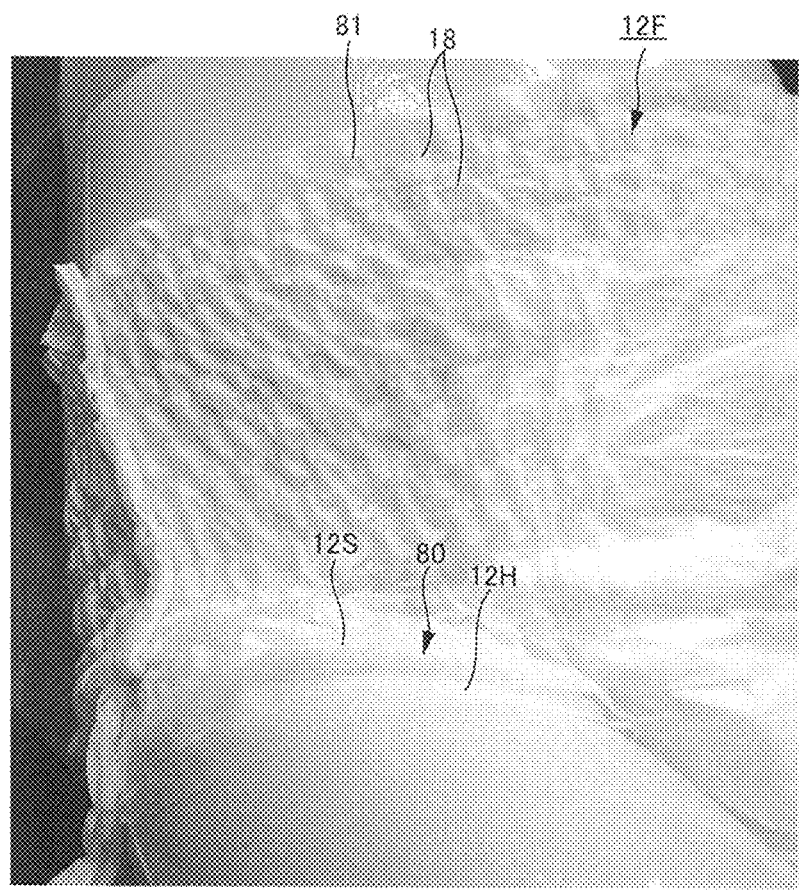
FIG. 9 is a photograph of the product sample put on the dummy doll.

Accordingly, the first sheet material 12S and the second sheet material 12H can be joined up to the waist edges of the ventral side outer body 12F and the dorsal side outer body 12B, which makes it possible to provide the resilient and elastic members 17 and 18 at the waist end portions of the ventral side outer body 12F and the dorsal side outer body 12B and prevent reduction in the fit of the waist end portions as illustrated in FIGS. 8 and 9. In addition, for the same reason, it is possible to prevent degradation in appearance caused by the spread of the first sheet material 12S and the second sheet material 12H at the waist end portions and deterioration in fit caused by inward folding of the waist end portions when the user is wearing the diaper as illustrated in FIGS. 8 and 9. Meanwhile, in the manufactured underpants-type disposable diaper, the non-joined portions 80 of the first sheet material 12S and the second sheet material 12H are positioned at the end portions of the leg openings in the ventral side outer body 12F and the dorsal side outer body 12B as illustrated in FIGS. 8 and 9. These end portions are positioned around the legs of the wearer and are essential to have following capability and flexibility in response to the wearer's large motion unlike the waist-side end portions. Accordingly, the presence of the non-joined portions 80, that is, the presence of the portions not hardened by joining is conversely advantageous. This makes it possible to obtain the effect of alleviating rash and abrasion in the wearer's body caused by contact.

Figure 10:
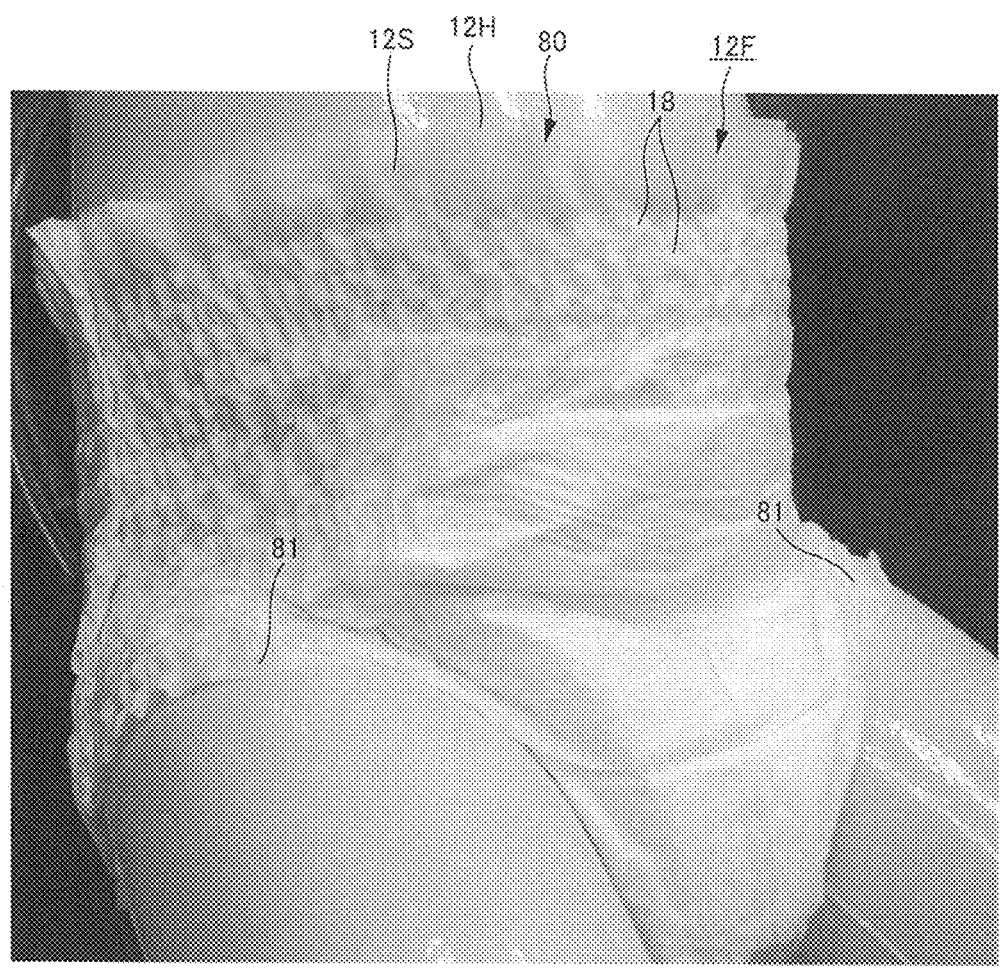
FIG. 10 is a photograph of the product sample put on the dummy doll.
Figure 11:
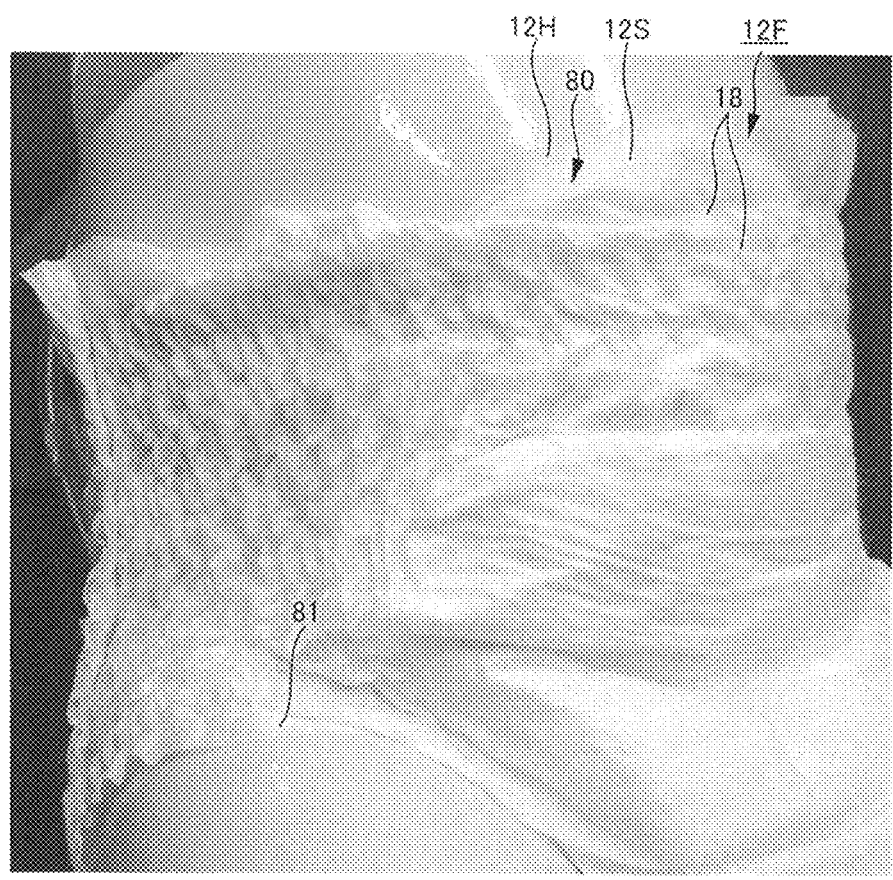
FIG. 11 is a photograph of the product sample put on the dummy doll.

In contrast, when the arrangements of the divided elastic belts 12f and 12b are not changed, the non-joined portions 80 are positioned at the waist end portions of the ventral side outer body 12F and the dorsal side outer body 12B as illustrated in FIGS. 10 and 11. Accordingly, it is not possible to provide resilient and elastic members 17 and 18 at the waist end portions, thereby resulting in insufficient fit of the waist end portions. In addition, in that case, the first sheet material 12S and the second sheet material 12H spread out at the non-bonded portions of the waist end portions to degrade appearance, and the non-joined portions 80 of the waist end portions are folded inward when the user is wearing the diaper, which may deteriorate the fit of the diaper as illustrated in FIG. 11.

<About the Underpants-Type Disposable Diaper>

Next, a structure of and materials for the diaper manufactured by the foregoing manufacturing method will be described. That is, the underpants-type disposable diaper illustrated in FIGS. 3 to 7 is manufactured by the foregoing manufacturing method. The underpants-type disposable diaper has the ventral side outer body 12F covering the ventral side of the wearer's waist and the dorsal side outer body 12B covering the dorsal side of the wearer's waist. The width-direction both side edges of the ventral side outer body 12F and the width-direction both side edges of the dorsal side outer body 12B are welded and joined together by heat sealing, ultrasound welding, or the like over the entire vertical overlapping parts of the two outer bodies to form a cylindrical waist part. Reference sign 12A represents side seal portions where the two outer bodies 12F and 12B are welded and joined. As in the illustrated example, when the dorsal side outer body 12B extends downward beyond the side seal portions 12A, the vertical area of the dorsal side outer body 12B including this extending part can be integrally subjected to heat sealing or the like.

In addition, the inner body 200 is provided from the width-direction central part in the inner surface of the ventral side outer body 12F to the width-direction central part in the inner surface of the dorsal side outer body 12B in the waist part. The ventral side outer body 12F and the dorsal side outer body 12B are not continuous but are separated from each other on the crotch side. The distance of the separation can be about 150 to 250 mm in the vicinities of the width-direction both side edges of the inner body 200.

The upper opening of the waist part constitutes the waist opening through which the wearer's waist passes. The parts on the width-direction both sides of the inner body 200 surrounded by a lower edge 12e of the waist part and the side edges of the inner body 200 constitute leg openings. In the state opened by peeling off the side seal portions 12A, the diaper has the shape as illustrated in FIG. 3. The inner body 200 extends and covers from the dorsal side through the crotch portion to the ventral side. The inner body 200 receives excrement, and absorbs and retains moisture. The waist part supports the inner body 200 on the wearer's body.

(Outer Body)

Figure 7:
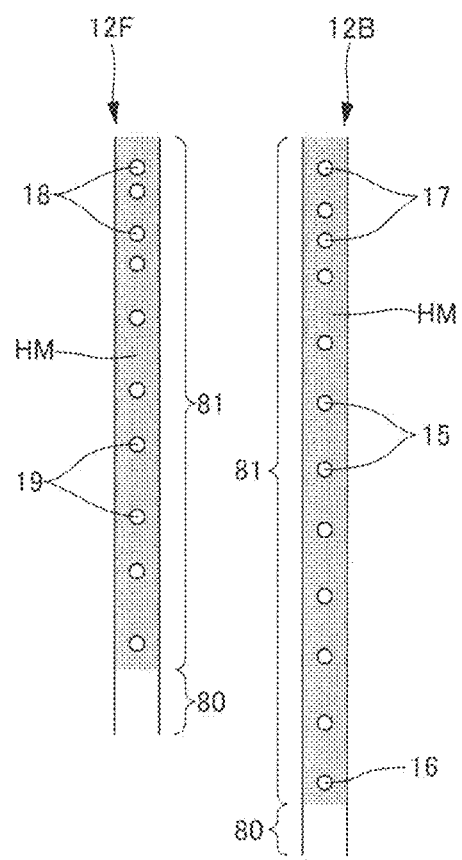
FIG. 7 is a cross-sectional view of FIG. 5 taken along line 7-7.

The ventral side outer body 12F and the dorsal side outer body 12B are formed by adhering the first sheet material 12S (composed of a sheet material 12Z) and the second sheet material 12H (composed of a CD direction outer part of the three-dimensional gathers 60) that extend from the waist-side edges to the leg opening-side edges without being folded as also illustrated in FIG. 7. Although there is no limitation on the material for the layers, non-woven fabric is preferred. There is no particular limitation on the raw fibers of the non-woven fabric. For example, the raw fibers may be synthetic fibers based on olefin such as polyethylene and polypropylene, polyester, or polyamide, reproduced fibers of rayon or cupra, natural fibers of cotton or the like, mixed fibers or composite fibers of two or more of the foregoing fibers. The non-woven fabric may be produced by any processing method. For example, the non-woven fabric may be spun-laced non-woven fabric, spun-bonded non-woven fabric, SMS non-woven fabric, melt-blown non-woven fabric, needle-punched non-woven fabric, thermal-bonded non-woven fabric, air-through non-woven fabric, point-bonded non-woven fabric, or the like. In particular, spun-bonded non-woven fabric and SMS non-woven fabric are preferred for their excellent strength and adhesion to the resilient members. In the case of using non-woven fabric, its basis weight is preferably about 10 to 40 g/m$^2$, more preferably about 10 to 22 g/m$^2$.

To enhance the fit around the wearer's waist, the elongated resilient and elastic members 15 to 19 composed of rubber threads or the like are sandwiched in a predetermined extended state and fixed by a hot-melt adhesive or the like between the first sheet material 12S and the second sheet material 12H in the two outer bodies 12F an 12B. The elongated resilient and elastic members 15 to 19 may be made of synthetic rubber or natural rubber. The first sheet material 12S and the second sheet material 12H in the outer bodies 12F and 12B can be bonded to each other and the elongated resilient and elastic members 15 to 19 can be sandwiched and fixed between the first sheet material 12S and the second sheet material 12H by the means of hot-melt adhesion, heat sealing, or ultrasound adhesion.

More specifically, the dorsal side outer body 12B has a main body part 13 that occupies the same vertical area as the side seal portions by the welding part 12A group and an extension part 14 that extends downward from the main body part 13. The extension part 14 has a width-direction central portion 14M overlapping the inner body 200 and cover portions 14C extending from the both sides of the width-direction central portion 14M.

The shape of the extension part 14 can be arbitrarily decided. The extension part 14 is rectangular in the illustrated example of FIGS. 3 to 7. However, cutting the leg opening-side edges of the extension part 14 in a curve shape along the legs would make the diaper favorable in appearance both in the product state and the worn state.

The dimensions of the extension part 14 can be arbitrarily decided. However, it is preferred that the width-direction length of the cover portions 14C (the width-direction maximum separation distance between lower edges 12e of the cover portions 14C and the side edges of the inner body 200) is 80 to 160 mm and the vertical length of the cover portions 14C (extension length) is 30 to 80 mm. In the case of forming the lower edges 12e of the cover portions 14C in a curve shape as in second and third embodiments described later, when the area of the square determined by the width-direction largest portion and the vertically largest portion of the extension part 14 is designated as S, the area of the extension part 14 is appropriately set to be 20 to 80%, in particular about 40 to 60% of S.

The main body part 13 can be conceptually divided in the vertical direction into a waist portion W and a lower waist portion U under the waist portion W. In general, when there are boundaries in the main body part 13 with changes in width-direction expansion and contraction stress (for example, changes in the thickness or extension ratio of the resilient and elastic members), the portion nearer a waist opening WO than the boundary nearest the waist opening WO constitutes the waist portion W. When there are no boundaries, the portion nearer the waist opening WO than the absorber 56 or the inner body 200 constitutes the waist portion W. Although the coverage of the waist portion W varies depending on the product size, the vertical length of the waist portion W can be 15 to 80 mm and the vertical length of the lower waist portion U can be 35 to 220 mm in general.

In the upper end portion (waist portion) W of the main body part 13, a plurality of dorsal side waist portion resilient and elastic members 17 are continuously fixed between the first sheet material 12S and the second sheet material 12H over the entire width at vertical intervals in the state extended in the width direction at a predetermined extension ratio. Of the dorsal side waist portion resilient and elastic members 17, one or more arranged in the region adjacent to the lower waist portion U of the main body part 13 may overlap the inner body 200 or may be provided only on the width-direction both sides of the width-direction central part overlapping the inner body 200. As the dorsal side waist resilient and elastic members 17, about 3 to 22 rubber threads with a thickness of about 300 to 1240 dtex, in particular about 470 to 940 dtex are preferably fixed at intervals of 4 to 12 mm and at an extension ratio of about 150 to 400%, in particular about 220 to 320%. The dorsal side waist portion resilient and elastic members 17 may not necessarily be equal in thickness or extension ratio. For example, the thickness and extension ratio of the resilient and elastic members may be different between the upper and lower sides of the dorsal side waist portion.

In the lower waist portion U of the main body part 13, a plurality of lower waist portion resilient and elastic members 15 is continuously fixed over the entire width between the first sheet material 12S and the second sheet material 12H on the upper side and width-direction both sides of the width-direction central part overlapping the inner body 200 at vertical intervals in the state extended along the width direction at a predetermined extension ratio. As the lower waist portion resilient and elastic members 15, about 5 to 30 rubber threads with a thickness of 300 to 1240 dtex, in particular about 470 to 940 dtex are preferably fixed at intervals of 1 to 15 mm, in particular 3 to 8 mm and at an extension ratio of about 200 to 350%, in particular about 240 to 300%.

In addition, in the extension part 14, a plurality of extension part resilient and elastic members 16 is continuously fixed over the entire width (at least over the entire cover portion 14C) between the first sheet material 12S and the second sheet material 12H at the width-direction both sides of the width-direction central part overlapping the inner body 200 at vertical intervals in the state extended along the width direction at a predetermined extension ratio. As the extension part resilient and elastic members 16, about 2 to 10 rubber threads with a thickness of about 300 to 1240 dtex, in particular about 470 to 940 dtex are preferably fixed at intervals of 5 to 40 mm, in particular 5 to 20 mm and at an extension ratio of 150 to 300%, in particular 180 to 260%.

Meanwhile, the ventral side outer body 12F is composed of a main body part (occupying the same vertical range as the side seal portions 12A composed of welding part group) in the basically same manner as the main body part 13 of the dorsal side outer body 12B. The ventral side outer body 12F has a rectangular shape extending along the waist and does not have the extension part 14 as in the dorsal side outer body 12B.

Specifically, out of the upper end portion (waist portion) W and the lower waist portion U of the ventral side outer body (main body part) 12F, in the waist portion W, a plurality of ventral side waist portion resilient and elastic members 18 is continuously fixed over the entire width between the first sheet material 12S and the second sheet material 12H at vertical intervals in the state extended in the width direction at a predetermined extension ratio. The ventral side waist portion resilient and elastic members 18 are preferably close to the dorsal side waist portion resilient and elastic members 17 in number, thickness, extension ratio, interval, and vertical arrangement as much as possible, but may be different. When they are different, the difference in number is 6 or less, preferably 3 or less, the difference in thickness is 450 dtex or less, preferably 300 dtex or less, the difference in extension ratio is 100% or less, preferably 40% or less, and the difference in interval is 10 mm or less, preferably 5 mm or less.

In the lower waist portion U of the ventral side outer body 12F (main body part), a plurality of lower waist portion resilient and elastic members 19 is continuously fixed over the entire width between the first sheet material 12S and the second sheet material 12H at the upper side and width-direction both sides of the width-direction central part overlapping the inner body 200 at vertical intervals in the state extended along the width direction at a predetermined extension ratio. The vertical arrangement area of the lower waist portion resilient and elastic members 19 may be only a portion of the lower part but is preferably the substantially entirety (the entire area on which their stretch force acts).

The lower waist portion resilient and elastic members 19 are preferably close to the lower waist portion resilient and elastic members 15 in number, thickness, extension ratio, interval, and vertical arrangement as much as possible, but may be different. When they are different, the difference in number is 10 or less, preferably 5 or less, the difference in thickness is 450 dtex or less, preferably 300 dtex or less, the difference in extension ratio is 100% or less, preferably 40% or less, and the difference in interval is 10 mm or less, preferably 5 mm or less.

The ventral side outer body 12F illustrated in the drawing is composed of only the part occupying the same vertical range as the side seal portions 12A. Alternatively, as with the dorsal side, the ventral side outer body 12F may be composed of the main body part 13 occupying the same vertical range as the side seal portions 12A and the extension part 14 extending downward from the main body part 13 (refer to the second and third embodiments described later). Accordingly, the ventral side outer body 12F can be shaped around the leg parts to fit to the wearer's groin. In this case, the area and front-back length of the extension part 14 are preferably 10 to 80%, more preferably 20 to 50% of the area and front-back length of the extension part 14. The extremely large extension part 14 would preferably lose a proper fit.

Meanwhile, when the resilient and elastic members 15, 16, and 19 are provided only on the width-direction both sides of the width-direction central part overlapping the inner body 200 as in the illustrated mode, the inner body 200 and the outer bodies 12F and 12B are preferably less prone to separate from each other. This mode may be the mode in which there are the resilient and elastic members only on the width-direction both sides, or may be the mode in which there are the resilient and elastic members across the inner body 200 from one side to the other side in the width-direction but the resilient and elastic members are cut at the width-direction central part overlapping the inner body 200 so that no stretching force acts (this is substantially equivalent to the absence of the resilient and elastic members). Alternatively, some or all of the resilient and elastic members 15, 16, and 19 may be provided across the inner body 200 from one side to the other side in the width-direction such that their stretching force acts on the entire main body part 13 and extension part 14 in the width direction.

(Joining the Sheet Materials in the Outer Bodies)

Characteristically, the leg opening-side end portions of the ventral side outer body 12F and the dorsal side outer body 12B do not have the resilient and elastic members 15 to 19 between the first sheet material 12S and the second sheet material 12H but constitute the non-joined portions 80 in which the first sheet material 12S and the second sheet material 12H are not joined together. In addition, the waist-side end portions of the ventral side outer body 12F and the dorsal side outer body 12B have the resilient and elastic members 17 and 18 between the first sheet material 12S and the second sheet material 12H and constitute the joined portions 81 in which the waist-side edges of the first sheet material 12S and the second sheet material 12H are aligned and the first sheet material 12S and the second sheet material 12H are joined together up to the waist-side edges. The non-joined portions 80 at the leg opening-side end portions and the joined portions 81 at the waist-side end portions respectively correspond to the non-joined portions 80 and the joined portions 81 that are formed at the step of forming the elastic belt 12 in the manufacturing method described above.

The joined portions 81 are desirably provided over the entire parts of the ventral side outer body 12F and the dorsal side outer body 12B except for the leg opening-side end portions to be the non-joined portions 80. However, the joined portions 81 may be provided only at the waist-side end portions and other parts may not be joined. For example, as described above in relation to the manufacturing method, the joined portions 81 may be provided continuously or intermittently in the MD direction and continuously or intermittently in the CD direction. In the illustrated example of FIG. 3, of the ventral side outer body 12F and the dorsal side outer body 12B, the dot-patterned portions are the joined portions 81, and the non-dot-patterned portions are the non-joined portions 80.

In this underpants-type disposable diaper, the first sheet material 12S and the second sheet material 12H are joined up to the waist edges of the ventral side outer body 12F and the dorsal side outer body 12B. This makes it possible to provide the resilient and elastic members 17 and 18 at the waist end portions of the ventral side outer body 12F and the dorsal side outer body 12B, and prevent reduction in the fit of the waist end portions as illustrated in FIGS. 8 and 9. In addition, for the same reason, it is possible to prevent degradation in appearance caused by the spread of the first sheet material 12S and the second sheet material 12H at the waist end portions and deterioration in fit caused by inward folding of the waist end portions when the user is wearing the diaper as illustrated in FIGS. 8 and 9. Meanwhile, the leg opening-side end portions of the ventral side outer body 12F and the dorsal side outer body 12B constitute the non-joined portions 80, as illustrated in FIGS. 8 and 9. These end portions are positioned around the legs of the wearer and are essential to have following capability and flexibility in response to the wearer's large motion unlike the waist-side end portions. Accordingly, the presence of the non-joined portions 80, that is, the presence of the portions not hardened by joining is conversely advantageous. This makes it possible to obtain the effect of alleviating rash and abrasion in the wearer's body caused by contact.

The width (front-back length) of the non-joined portions 80 (leg opening-side end portions) can be arbitrarily decided. The width of the non-joined portions 80 is desirably larger from the viewpoint of enhancing the effect of alleviating rash and abrasion in the wearer's legs resulting from contact. However, the width of the non-joined portions 80 is desirably about 3 to 50 mm because the non-joined portions 80 with a width of more than 50 mm in the diaper for adults who are generally thick in legs and large in range of motion may be folded inward to deteriorate the fit. In addition, the width of the non-joined portions 80 is more desirably 5 to 15 mm taking into account the diaper for babies and infants who are generally thinner in legs and smaller in range of motion.

Meanwhile, when the non-joined portions 80 are provided at the waist end portions of the ventral side outer body 12F and the dorsal side outer body 12B, the resilient and elastic members 17 and 18 cannot be provided at the waist end portions as illustrated in FIGS. 10 and 11, whereby the fit of the waist end portions becomes insufficient. In addition, in that case, the first sheet material 12S and the second sheet material 12H spread out at the non-bonded portions of the waist end portions to degrade appearance, and the non-joined portions 80 of the waist end portions are folded inward when the user is wearing the diaper as illustrated in FIG. 11, which may deteriorate the fit of the diaper.

(Inner Body)

Figure 4:
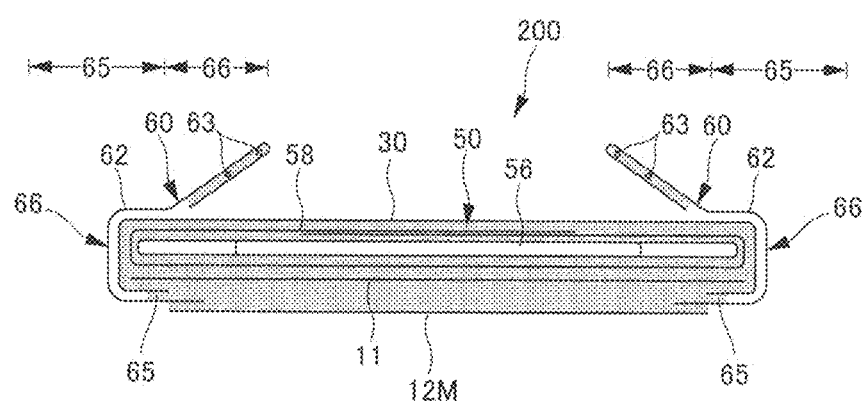
FIG. 4 is a cross-sectional view of FIG. 3 taken along line 4-4.

The inner body 200 is rectangular in the illustrated example but may have an arbitrary shape. As illustrated in FIG. 4, the inner body 200 includes a top sheet 30 on the body side, a liquid-impervious sheet 11, and an absorbent element 50 intervening between the top sheet 30 and the liquid-impervious sheet 11. The outer body for inner body 12M is provided on the back side of the liquid-impervious sheet 11 to cover the back surface of the inner body 200. Further, to prevent excretion from leaking to the both sides of the inner body 200, the three-dimensional gathers 60 erecting toward the wearer's body are provided on the both sides of the inner body 200. Although not illustrated, the components of the inner body 200 can be fixed to one another as appropriate by solid, bead, or spiral application of a hot-melt adhesive or the like.

(Top Sheet)

The top sheet 30 is pervious to liquid and may be a porous or non-porous non-woven fabric or a porous plastic sheet, for example. There is no specific limitation on raw fibers for the non-woven fabric. For example, the raw fibers may be synthetic fibers based on olefin such as polyethylene and polypropylene, polyester, or polyamide, reproduced fibers of rayon, cupra, or the like, natural fibers of cotton or the like, and mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. For flexibility and drape properties, spun-bonding and spun-lacing are preferred. For bulkiness and softness, air-through processing, point-bonding, and thermal bonding are preferred.

The top sheet 30 may be composed of a single sheet or a layered sheet obtained by sticking two or more sheets to each other. Similarly, the top sheet 30 may be composed of a single sheet or two or more sheets in a planar direction.

(Interlayer Sheet)

To move the liquid having passed through the top sheet 30 quickly to the absorber, the interlayer sheet (also called as "second sheet") higher in liquid permeation speed than the top sheet 30 may be provided. The interlayer sheet can not only move the liquid quickly to the absorber with enhancement in absorption performance of the absorber but also prevent a "reflowing" phenomenon of the absorbed liquid from the absorber to keep the top sheet 30 in a dry state at any time. The interlayer sheet may not be provided.

The material for the interlayer sheet may be the same material as that for the top sheet 30, spun-laced, spun-bonded, SMS, or pulp non-woven fabric, mixture of pulp and rayon, point-bonded paper, or crepe paper. Among them, non-woven fabric is preferred for its excellent liquid perviousness. In particular, air-through non-woven fabric is preferred for its bulkiness. Core-sheath composite fibers are preferably used for the air-through non-woven fabric. The resin for use in the core may be polypropylene (PP) but is preferably polyester (PET) for its high rigidity. The basis weight is preferably 20 to 80 g/m$^2$, more preferably 25 to 60 g/m$^2$. The thickness of the raw fibers in the non-woven fabric is preferably 2.2 to 10 dtex. To make the non-woven fabric high in bulkiness, eccentric fibers with no core in the center, hollow fibers, or eccentric and hollow fibers are preferably used for some or all of the raw fibers.

The interlayer sheet is desirably shorter than the width of the absorber 56 and arranged in the center of the absorber 56, but may be provided over the entire width of the absorber 56. The longitudinal length of the interlayer sheet may be the same as the length of the absorber 56 or may fall within a shorter-length range centered on the area for receiving the liquid.

(Liquid-Impervious Sheet)

There is no particular limitation on the material for the liquid impervious sheet 11. For example, material for the liquid impervious sheet 11 may be a film material (waterproof film) formed from an olefin resin such as polyethylene or polypropylene, a laminate non-woven fabric sheet in which non-woven fabric is layered on a polyethylene sheet, a nonwoven fabric sheet in which a waterproof sheet intervenes to secure substantially liquid imperviousness (in this case, the waterproof sheet and the non-woven fabric constitute a liquid-impervious sheet), or the like. As a matter of course, other liquid-impervious and moisture-pervious materials having been used preferably in recent years from the viewpoint of stuffiness prevention may be used. The liquid-impervious and moisture-pervious material sheet may be a microporous sheet that is obtained by melting and kneading an inorganic filling agent in an olefin resin such as polyethylene, polypropylene, or the like, for example, to form a sheet and then elongating the sheet in a uniaxial or biaxial direction. Besides, the liquid-impervious sheet 11 may be a non-woven fabric sheet of microdenier fibers, or may be a liquid-impervious sheet that is formed, without the use of a waterproof film, by enhancing leak-proof performance by reducing the size of air gaps between fibers with the application of heat or pressure or by coating the sheet with a high-water absorption resin, a hydrophobic resin, or a water repellent agent.

In addition, a printed or colored design may be applied to the inner or outer surface of the liquid-impervious sheet 11. Further, a printed or colored design sheet may be stuck to the outside of the liquid-impervious sheet 11 as a member separated from the outer body for inner body 12M. Moreover, an excretion indicator to change in color due to absorption of liquid can be provided inside the liquid-impervious sheet 11.

(Three-Dimensional Gathers)

The three-dimensional gathers 60 are belt-like members extended entirely along the both sides of the inner body 200 in the front-back direction. The three-dimensional gathers 60 are provided to shut off urine or loose stool moving laterally over the top sheet 30 to prevent lateral leakage of the liquid. In this embodiment, the three-dimensional gathers 60 stand on the sides of the inner body 200. Each of the three-dimensional gathers 60 stands obliquely toward the central portion in the width direction at the base portion, and stands obliquely toward the outside in the width direction from the intermediate portion to the forward edge.

More specifically, each of the three-dimensional gathers 60 is formed in such a manner that a belt-like gather sheet 62 having the same length as the front-back length of the inner body 200 is folded back and overlapped in the width direction, and a plurality of elongated resilient and elastic members 63 is fixed to the sheet at the folded part and its neighborhood at width-direction intervals in the state extended along the longitudinal direction. Base portions opposite to tip portions (end portions opposite to the sheet folded parts in the width direction) of the three-dimensional gathers 60 are set as attachment parts 65 fixed to the back surface of the side edge parts of the inner body 200, and the parts other than the attachment parts 65 are set as protrusion parts 66 (folded part-side parts) protruding from the attachment parts 65. The illustrated example is linear contact-type three-dimensional gathers in which the protrusion parts 66 are not folded outward in the width direction. Alternatively, the three-dimensional gathers 60 may be surface contact-type three-dimensional gathers that are composed of base-side parts in which the protrusion parts 66 protrude toward the width-direction center and tip-side parts that are folded outward in the width direction from the tip of the base-side part. In addition, front-back both end portions 67 of the protrusion parts 66 are set as fallen portions 67 that are fixed in the fallen state to the side surface of the top sheet 30 by a hot-melt adhesive or heat seal, a front-back middle portion between the fallen portions 67 is set as a non-fixed free portion, and the elongated resilient and elastic members 63 are fixed to the free portion in the extended state in the front-back direction.

The gather sheet 62 may be preferably formed by applying a water repellent treatment with silicone or the like as necessary to flexible non-woven fabric excellent in uniformity and concealing performance such as spun-bonded non-woven fabric (SS, SSS, or the like), SMS non-woven fabric (SMS, SSMMS, or the like), and melt-blown non-woven fabric. The basis weight of the fibers is preferably about 10 to 30 g/m$^2$. The elongated resilient and elastic members 63 may be rubber threads or the like. In the case of using spandex rubber threads, the fineness of the threads is preferably 470 to 1240 dtex, more preferably 620 to 940 dtex. The extension ratio of the threads at the time of fixing is preferably 150 to 350%, more preferably 200 to 300%.

The number of elongated resilient and elastic members 63 provided in the free portions of the three-dimensional gathers 60 is preferably 2 to 6, more specifically 3 to 5. The arrangement spacing 60d is appropriately 3 to 10 mm. According to this configuration, the diaper is likely to touch the skin by surface with arrangement of the elongated resilient and elastic members 63. The elongated resilient and elastic members 63 may be arranged not only at the edge portions but also at the base portions.

The attachment portions 65 of the three-dimensional gathers 60 may be fixed to appropriate members in the inner body 200 such as the top sheet 30, the liquid impervious sheet 11, and the absorbent element 50.

In the thus configured three-dimensional gathers 60, the contraction force of the elongated resilient and elastic members 63 acts to make the both end portions in the front-back direction closer to each other. The both end portions of the protrusions 66 in the front-back direction are fixed so as not to stand, whereas the middle portions between the both ends of the protrusions 66 are non-fixed free portions. Accordingly, only the free portions stand to touch the wearer's body as illustrated in FIG. 4. In particular, when the attachment portions 65 are positioned on the back surface of the inner body 200, the three-dimensional gathers 60 stand and open outward in the width direction at the crotch portion and its neighborhood. Accordingly, the three-dimensional gathers 60 are brought into surface contact around the legs to produce an improved fit.

Unlike the illustrated form, the three-dimensional gathers may be provided doubly (in two rows) at each of the right and left sides of the inner body 200.

(Absorbent Element)

The absorbent element 50 has an absorber 56 and a wrapping sheet 58 that wraps at least the back surface and side surfaces of the absorber 56. The wrapping sheet 58 may be omitted.

(Absorber)

The absorber 56 may be formed from a fiber assembly. The fiber assembly may be fluff pulp fibers or accumulated short fibers such as synthetic fibers, or a filament assembly obtained by opening tows (fiber bundles) of synthetic fibers such as cellulose acetate, as necessary. The basis weight of fluff pulp or accumulated short fibers may be about 100 to 300 g/m$^2$, and the basis weight of a filament assembly may be about 30 to 120 g/m$^2$, for example. The fineness of synthetic fibers is, for example, 1 to 16 dtex, preferably 1 to 10 dtex, more preferably 1 to 5 dtex. In the case of a filament assembly, the filaments may be non-crimped fibers but are preferably crimped fibers. The number of crimps in the crimped fibers may be, for example, about 5 to 75 per inch, preferably about 10 to 50 per inch, more preferably about 15 to 50 per inch. The crimped fibers are evenly crimped in many cases. High-absorbent polymer particles are preferably dispersed and held in the absorber 56.

The absorber 56 may be rectangular in shape but preferably has an hourglass shape having a front end portion 56F, a back end portion 56B, and a narrower portion 56N that is positioned between the front end portion 56F and back end portion 56B and is narrower than the two end portions as illustrated in FIG. 3 to improve the absorber 56 and the three-dimensional gathers 60 in a fit of the edges around the legs.

The dimensions of the narrower part 56N can be arbitrarily decided. The smallest width of the narrower part 56N is preferably set to about 0.55 to 0.70 times larger the entire width of the absorber 56. The front-back length of the narrower part 56N is preferably set to about 25 to 50% of the entire length of the absorber 56.

(High-Absorbent Polymer Particles)

The high-absorbent polymer particles include "particles" and "powder". The diameter of the high-absorbent polymer particles may be the same as that of general particles for use in this type of absorbent article, and is desirably 1000 μm or less, in particular 150 to 400 μm. There is no particular limitation on the material for the high-absorbent polymer particles but the material preferably has a water absorption capacity of 40 g/g or more. The high-absorbent polymer particles may be based on starch, cellulose, or synthetic polymer. The high-absorbent polymer particles may be made of a starch-acrylate graft copolymer, a saponified substance of starch-acrylonitrile copolymer, a crosslinking substance of sodium carboxymethylcellulose, an acrylate polymer, or the like. The high-absorbent polymer particles are preferably used in a general particulate form but may be used in another form.

The water absorption rate of the high-absorbent polymer particles is preferably 40 seconds or less. At a water absorption rate of more than 40 seconds, the absorbed liquid is more likely to flow back from the absorber 56 to the outside of the absorber 56 (so called "reflowing").

The basis weight of the high absorbent polymer particles can be decided as appropriate depending on the absorption volume required in the use of the absorber 56. Therefore, although being not specified absolutely, the basis weight may be 50 to 350 g/m$^2$. When the basis weight of the polymer is lower than 50 g/m$^2$, it is hard to assure the absorption volume. When the basis weight of the polymer exceeds 350 g/m$^2$, the effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion region than the other regions. With regard to gender differences, the dispersing density (quantity) of the high-absorbent polymer particles may be increased at the front side of the product for male, and may be increased at the central part of the product for female. In addition, the polymer may not be provided locally (in spots for example) in the absorber 56 in the planar direction.

(Wrapping Sheet)

In the case of using the wrapping sheet 58, the material for the wrapping sheet 58 may be a paper material such as tissue paper and crepe paper, non-woven fabric, polyethylene-laminated non-woven fabric, a porous sheet, or the like. However, the material sheet is desirably configured to retain the high-absorbent polymer particles. In the case of using non-woven fabric instead of crepe paper, the hydrophilic SMMS (spun-bonded/melt-blown/melt-blown/spun-bonded) non-woven fabric is preferred in particular and its material may be polypropylene, polyethylene/polypropylene, or the like. The basis weight of the material is desirably 5 to 40 g/m$^2$, in particular 10 to 30 g/m$^2$.

The wrapping sheet 58 may be configured to wrap the entire absorber 56 or wrap only the back surface and side surfaces of the layers in the absorber 56. In addition, although not illustrated in the drawing, the wrapping sheet 58 may be configured to cover the upper surface and side surfaces of the absorber 56 by crepe paper or non-woven fabric and cover the lower surface of the absorber 56 by a liquid-impervious sheet of polyethylene or the like, or may be configured to cover the upper surface of the absorber 56 by crepe paper or non-woven fabric and cover the side surfaces and the lower surface of the absorber 56 by a liquid-impervious sheet of polyethylene or the like (these materials constitute the components of the wrapping sheet). As necessary, the wrapping sheet 58 may be configured to sandwich the absorber 56 between the two upper and lower sheets of the wrapping sheet 58 or position the absorber 56 only on the lower surface of the wrapping sheet 58.

(Outer Body for Inner Body)

The outer body for inner body 12M constituting the outer surface of the product is provided on the back surface of the inner body 200. The material for the outer body for inner body 12M can be the same as the material for the outer body (for example, the first sheet material 12S).

Figure 5:
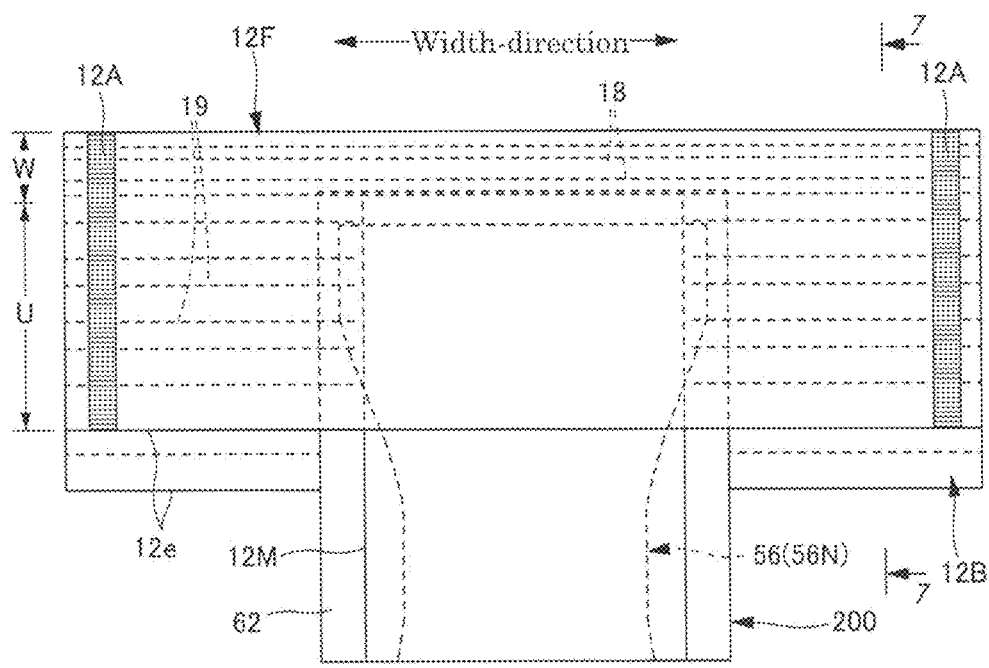
FIG. 5 is a front view of the product in the opened state.
Figure 6:
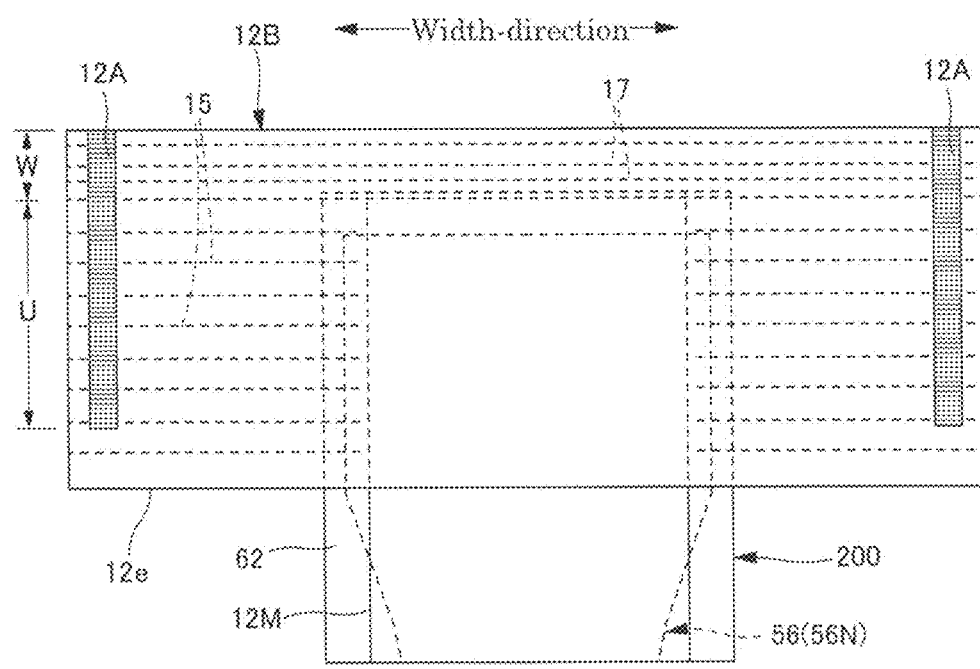
FIG. 6 is a rear view of the product in the opened state.

The front-back length of the outer body for inner body 12M may be equal to or smaller than that of the inner body 200. The width of the outer body for inner body 12M may be equal to or different from the width of the inner body 200. In particular, when the width of the outer body for inner body 12M is smaller than the width of the inner body 200, the side edges of the outer body for inner body 12M are separated from the side edges of the inner body 200 toward the width-direction central side as illustrated in FIGS. 4 to 6. Accordingly, even when the wearer's legs get rubbed against the side edges of the inner body 200, the side edges of the outer body for inner body 12M does not contact the legs or cause irritation of the skin. In addition, when the outer body for inner body 12M is stuck to the inner body 200, the inner body 200 becomes hardened under the influence of the adhesion means (for example, an adhesive). However, when the side edges of the outer body for inner body 12M are separated from the side edges of the inner body 200 toward the width-direction central side, the side parts of the inner body 200 do not become hardened but can come into soft contact with the legs. In general cases, the width of the outer body for inner body 12M is desirably set to about 70 to 95% of the width of the inner body 200.

<Descriptions of the Terms Used Herein>

Unless otherwise specified herein, the terms used herein have the meanings described below.

"front-back (vertical) direction" refers to the direction linking the ventral side (front side) and the dorsal side (back side), and the "width direction" refers to the direction (right-left direction) orthogonal to the front-back direction. The "up-down direction" refers to the direction that becomes orthogonal to the waist direction when the diaper is worn, that is, when the diaper is folded into two at the crotch portion such that the front panel and the back panel are overlapped at the both sides, in other words, the direction linking a waist opening and a crotch portion.

The "extension ratio" refers to a value with respect to 100% representing the natural length.

The "basis weight" is measured as described below. A specimen or a test piece is preliminarily dried and left stand in a test room or a test device in a standard state (a place of test shall be at a temperature of 20±5° C. and a relative humidity of 65% or less) until reaching a constant weight. The preliminary drying refers to turning the specimen or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (+2 mm) specimen by the use of a basis weight plate (200 mm×250 mm±2 mm) The weight of the specimen is measured and the measured value is multiplied by 20 to determine the weight per square meter as a basis weight.

The "thickness" is automatically measured by an automated thickness gauge (KES-G5 handy compression measurement program) on the conditions that the load is 10 gf/cm$^2$ and the pressure area is 2 cm$^2$.

INDUSTRIAL APPLICABILITY

The present invention can be used for underpants-type disposable diapers and manufacturing methods thereof as in the foregoing examples.

REFERENCE SIGNS LIST

11 Liquid-impervious sheet
12 Elastic belt
12B Dorsal side outer body
12F Ventral side outer body
12H Second sheet material
12M Outer body for inner body
12S First sheet material
12*f* and 12*b* Divided elastic belts
15 to 19 Resilient and elastic members
30 Top sheet
50 Absorbent element
56 Absorber
58 Wrapping sheet
60 Three-dimensional gather
62 Gather sheet
70 Hot-melt adhesive
80 Non-joined portion
81 Joined portion
200 Inner body
501 Elastic belt formation step
502 Resilient and elastic member cutting step
503 Elastic belt division and arrangement changing step
504 Inner body attachment step
505 Side part joining step
506 Cutoff step
603 Inner body cutoff device
604 Joining device
605 Diaper cutoff device
606 Outer body for inner body attachment roll

The invention claimed is:

1. A method for manufacturing an underpants-type disposable diaper comprising:
  an outer body that is formed by joining both side parts of a ventral side outer body and both side parts of a dorsal side outer body; and
  an inner body that has a front part joined to a width-direction central area of the ventral side outer body and a back part joined to a width-direction central area of the dorsal side outer body respectively and passes through a crotch portion of a wearer, the ventral side outer body and the dorsal side outer body being not continued but separated at a crotch side, wherein a belt-like continuous first sheet material is supplied in a direction of continuity thereof, resilient and elastic members for imparting elasticity to the ventral side outer body and the dorsal side outer body are disposed on the first sheet material, a belt-like continuous second sheet material is supplied in a direction of continuity thereof on the resilient and elastic members in the first sheet material to sandwich the resilient and elastic members between the first sheet material and the second sheet material, and overlapping areas of the first sheet material and the second sheet material are not joined together at CD direction both end portions but are joined together at an area between the both end portions to form a belt-like continuous elastic belt, the elastic belt is cut in the middle of a CD direction thereof at a joined position of the first sheet material and the second sheet material to form a pair of divided elastic belt, and CD direction positions of these divided elastic belts are exchanged or the divided elastic belts are vertically reversed respectively, and the diaper is manufactured such that one of the pair of divided elastic belts is set as the ventral side outer body and the other is set as the dorsal side outer body.

2. The method for manufacturing an underpants-type disposable diaper according to claim 1, wherein the first sheet material and the second sheet material are joined together by a hot-melt adhesive.

3. The method for manufacturing an underpants-type disposable diaper according to claim 1, wherein the first sheet material and the second sheet material are equal in CD direction width.

4. An underpants-type disposable diaper comprising:
an outer body that is formed by joining both side parts of a ventral side outer body and both side parts of a dorsal side outer body; and
an inner body that has a front part joined to a width-direction central area of the ventral side outer body and a back part joined to a width-direction central area of the dorsal side outer body and passes through a crotch portion of a wearer, the ventral side outer body and the dorsal side outer body being not continued but separated at a crotch side,
wherein the ventral side outer body and the dorsal side outer body have a first sheet material and a second sheet material that extend from their waist-side edges to leg opening edges without being folded and resilient and elastic members that are provided between the first sheet material and the second sheet material,
at leg opening-side end portions of the ventral side outer body and the dorsal side outer body, the resilient and elastic members are not provided between the first sheet material and the second sheet material, and portions of the first sheet material and the second sheet material that are not joined together form non-joined portions, a CD direction width of the non-joined portions is 3 to 50 mm, and
at waist-side end portions of the ventral side outer body and the dorsal side outer body, the resilient and elastic members are provided between the first sheet material and the second sheet material, the waist-side edges of the first sheet material and the second sheet material coincide with each other, and the first sheet material and the second sheet material are joined up to the waist-side edges.

5. The underpants-type disposable diaper according to claim 4, wherein the joining is made by a hot-melt adhesive.

* * * * *